United States Patent
Kim et al.

(10) Patent No.: US 8,753,285 B2
(45) Date of Patent: Jun. 17, 2014

(54) ECG SENSING APPARATUS AND METHOD FOR REMOVAL OF BASELINE DRIFT

(71) Applicant: Korea Electronics Technology Institute, Seongnam-si (KR)

(72) Inventors: Young Hwan Kim, Yongin-si (KR); Jae Gi Son, Yongin-si (KR); Dong Sun Kim, Seongnam-si (KR); Seung Chul Lee, Yangsan-si (KR)

(73) Assignee: Korea Electronics Technology Institute, Seongnam-Si, Gyeonggi-Do (KR)

( * ) Notice: Subject to any disclaimer, the term of this patent is extended or adjusted under 35 U.S.C. 154(b) by 0 days.

(21) Appl. No.: 14/025,319

(22) Filed: Sep. 12, 2013

(65) Prior Publication Data

US 2014/0100465 A1    Apr. 10, 2014

(30) Foreign Application Priority Data

Oct. 5, 2012    (KR) .................. 10-2012-0110506

(51) Int. Cl.
*A61B 5/02*    (2006.01)

(52) U.S. Cl.
USPC ........................................................ 600/508

(58) Field of Classification Search
CPC ...................................................... A61B 5/0452
USPC .................................................. 600/508, 509
See application file for complete search history.

(56) References Cited

U.S. PATENT DOCUMENTS

2007/0078353 A1*    4/2007    Holland .................... 600/509

FOREIGN PATENT DOCUMENTS

KR    100400213    11/2003

OTHER PUBLICATIONS

Korean Office Action for 10-2012-0110506 dated Oct. 18, 2013, citing the above reference(s).

* cited by examiner

*Primary Examiner* — Christopher D Koharski
*Assistant Examiner* — Nadia Ahmad
(74) *Attorney, Agent, or Firm* — Lowe Hauptman & Ham, LLP

(57) ABSTRACT

An ECG sensing apparatus and a method for removing a baseline drift in the clothing are provided. The ECG sensing apparatus filters ECG signals and filters a baseline drift noise which is caused by human body's motion and breathing. Accordingly, the baseline drift in the sensing apparatus is minimized even if there is a free motion.

6 Claims, 4 Drawing Sheets

ECG SENSING APPARATUS AND METHOD FOR REMOVAL OF BASELINE DRIFT

CROSS-REFERENCE TO RELATED APPLICATION

This application claims priority from Korean Patent Application No. 10-2012-0110506, filed on Oct. 5, 2012 in the Korean Intellectual Property Office, the disclosure of which is incorporated herein by reference in its entirety.

BACKGROUND

1. Field

Methods and apparatuses consistent with exemplary embodiments relate to an electrocardiogram (ECG) sensing apparatus, and more particularly, to an ECG sensing apparatus which is built in clothing.

2. Description of the Related Art

Convergence between small-scale personal area technologies and health care equipments enable medical health care monitoring to be performed on a real time basis, and thus is expected as a high value-added field that can accomplish treatment and diagnosis.

The small-scale personal area technologies include radio frequency identification (RFID), ultra wide band (UWB), Bluetooth, Zigbee, wireless sensor network, etc., and these technologies have been developed to replace wires in various fields and provide convenience to users.

As such, recent wearable health care documents or products have announced a biosensor node of a miniaturized wearable type that can measure ECG and photoplethysmograph (PPG) signals on a real time basis and transmit bio-signals using a local area network, or various related products have been released.

The ECG signals, which are the most representative of bio-signals, make it possible to extract a variety of bio-information such as a heartbeat, a stress index, a breathing rate, arrhythmia, etc., and thus may be regarded as an indicator for providing information such as patient's heart condition or normal health condition.

A health care system of such a bio-based wearable type may cause a baseline noise due to breathing and may cause a muscle sound which is generated by an effect of peripherals or patient's motion.

In particular, motion artifacts may be caused by a change in the impedance of electrodes when a user wears the electrodes and walks, runs, or breathes. Such a noise may frequently appear when the ECG signals are recorded, and it is difficult to analyze the signals and thus it is difficult to diagnose and analyze exactly without removing the noise appropriately.

As a solution to prevent the baseline drift, the ECG may be monitored using a high pass filter of a high cutoff frequency. However, in this case, there is a problem that an effective ECG signal is distorted.

In recent years, an adaptive filter is used to remove the baseline drift noise overlapping the ECG or PPG signals. This filter may show good performance, but should use an objective reference signal to remove a noise signal overlapping original signals.

However, when a wrong reference signal is used as input, no noise signal is removed or the ECG signal may be distorted. Also, since the baseline noise should be removed using a certain reference signal as input every time that a noise signal overlaps the ECG signal, it is not easy to require mobility.

SUMMARY

One or more exemplary embodiments may overcome the above disadvantages and other disadvantages not described above. However, it is understood that one or more exemplary embodiment are not required to overcome the disadvantages described above, and may not overcome any of the problems described above.

One or more exemplary embodiments provide an ECG sensing apparatus using a least mean square (LMS) algorithm-based adaptive linear prediction filter, which can minimize a baseline drift in a sensing apparatus even if there is a free motion, and a method thereof.

According to an aspect of an exemplary embodiment, there is provided an ECG sensing apparatus including: an ECG sensor configured to measure human body's ECG and generate an ECG signal; a pre-processor configured to perform filtering and amplification with respect to the ECG signal which is generated by the ECG sensor; an analog-digital converter (ADC) configured to convert the ECG signal which is output from the pre-processor from an analogue format into a digital format; a filter configured to filter the ECG signal applied by the ADC and filter a baseline drift noise which is caused by motion and breathing of the human body; and a communication module configured to wirelessly transmit the ECG signal which is filtered by the filter.

The filter may not use an additional reference signal other than the ECG signal that is input from the ADC.

The filter may include: an inputter configured to receive the ECG signal which is converted into the digital signal by the ADC; an adaptive linear prediction filter configured to remove the baseline drift noise which exists in the ECG signal input to the inputter; a buffer configured to temporarily store the filtered ECG signal which is output from the adaptive linear prediction filter; and an outputter configured to transmit the ECG signal temporarily stored in the buffer to the communication module.

The adaptive linear prediction filter may include: a sub delayer which includes a plurality of delayers configured to shift the ECG signals input to the inputter in sequence; a main delayer which includes a plurality of delayers configured to shift the ECG signals output from the sub delayers in sequence; a gain unit configured to multiply the ECG signals temporarily stored in the delayers of the main delayer by corresponding coefficients, and output the ECG signals; and an adder configured to add up all of the outputs of the gain unit and generate a filtered ECG signal.

A number of delayers provided in the sub delayer may be smaller than a number of delayers provided in the main delayer.

The adaptive linear prediction filter may further include: a subtractor configured to subtract the filtered ECG signal which is generated by the adder from the ECG signal input to the inputter, and generate an error signal; and a coefficient controller configured to update the coefficients of the gain unit using the error signal which is output from the subtractor and the ECG signals which are temporarily stored in the delayers of the main delayer.

The coefficient controller may update the coefficients of the gain unit using the following equation:

$$w[k] = w[k] + \mu \epsilon x[k+\text{delay}]$$

wherein $w[k]$ is a coefficient of a k-th amplifier of the gain unit, $\mu$ is a convergence constant, $\epsilon$ is an error signal, $x[k+\text{delay}]$ is an ECG signal which is temporarily stored in a k-th delayer of the main delayer, and delay is a number of delayers provided in the sub delayer.

According to an aspect of another exemplary embodiment, there is provided a method for sensing ECG, the method including: measuring human body's ECG and generating an ECG signal; pre-processing to perform filtering and amplification with respect to the ECG signal which is generated in the generating operation; converting the ECG signal which is output in the pre-processing operation from an analogue format into a digital format; filtering the ECG signal which is converted in the converting operation and filtering a baseline drift noise which is caused by motion and breathing of the human body; and wirelessly transmitting the ECG signal which is filtered in the filtering operation.

According to the exemplary embodiments as described above, the ECG sensing apparatus using the LMS algorithm-based adaptive linear prediction filter can minimize a baseline drift in the sensing apparatus even if there is a free motion. Also, the delayers are distinguished so that interrelationship between the noise of the ECG signal which is input to the adaptive linear prediction filter, and the noise of the ECG signals which are temporarily stored in the main delayer can be eliminated when the coefficient is updated.

BRIEF DESCRIPTION OF THE DRAWING FIGURES

The above and/or other aspects will be more apparent by describing in detail exemplary embodiments, with reference to the accompanying drawings, in which.

DETAILED DESCRIPTION OF EXEMPLARY EMBODIMENTS

Figure 1:
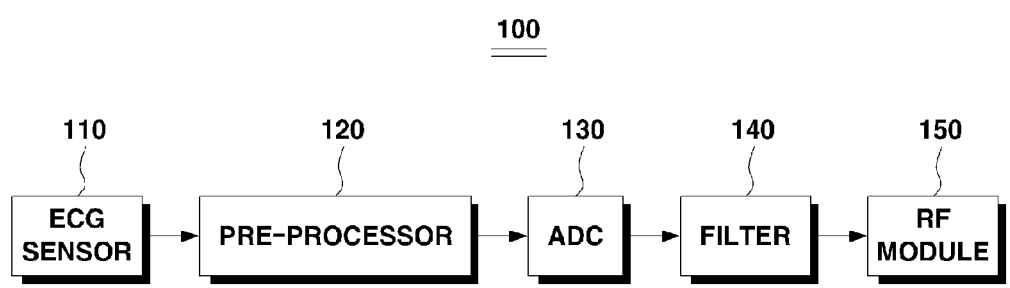
FIG. 1 is a block diagram illustrating an ECG sensing apparatus according to an exemplary embodiment.

Hereinafter, exemplary embodiments will be described in greater detail with reference to the accompanying drawings.

In the following description, same reference numerals are used for the same elements when they are depicted in different drawings. The matters defined in the description, such as detailed construction and elements, are provided to assist in a comprehensive understanding of exemplary embodiments. Thus, it is apparent that exemplary embodiments can be carried out without those specifically defined matters. Also, functions or elements known in the related art are not described in detail since they would obscure the exemplary embodiments with unnecessary detail.

FIG. 1 is a block diagram illustrating an ECG sensing apparatus according to an exemplary embodiment. The ECG sensing apparatus 100 according to an exemplary embodiment is an apparatus that measures an ECG signal on a real time basis, and has a limited processing ability but can remove a baseline noise from the ECG signal effectively.

Therefore, when the ECG sensing apparatus 100 is built in clothing, the ECG sensing apparatus 100 according to an exemplary embodiment can minimize motion artifacts. The ECG sensing apparatus 100 may be manufactured to be attachable to or detachable from clothing or a chest belt, and measured ECG information may be transmitted to a base station (not shown) through a relay node (not shown).

The ECG sensing apparatus 100, which performs the above-described function, includes an ECG sensor 110, a pre-processor 120, an analog-digital converter (ADC) 130, a filter 140, and a radio frequency (RF) module 150.

The ECG sensor 110, which is a conductive textile electrode, measures human body's ECG and generates an ECG signal, and transmits the generated ECG signal to the pre-processor 120.

The pre-processor 120 performs pre-processing such as amplification and filtering with respect to the ECG signal generated by the ECG sensor 110. Specifically, the pre-processor 120 removes a low frequency noise included in the ECG signal using a high pass filter (HPF), amplifies the ECG signal from which the low frequency noise has been removed, removes a high frequency noise included in the ECG signal using a low pass filter (LPF), amplifies the ECG signal from which the high frequency noise has been removed again, and outputs the ECG signal.

The ADC 130 converts the ECG signal which is output from the pre-processor 120 from an analogue format to a digital format, and applies the ECG signal to the filter 140.

The filter 140 filters the digital ECG signal which is applied by the ADC 130, and filters a baseline drift noise which is caused by motion and breathing of a user who wears the ECG sensing apparatus 100.

In particular, the filter 140 does not use an additional reference signal other than the input ECG signal. A configuration of the filter 140 will be explained in detail.

The RF module 150 wirelessly transmits the ECG signal which has been filtered by the filter 140 to the relay node.

Figure 2:
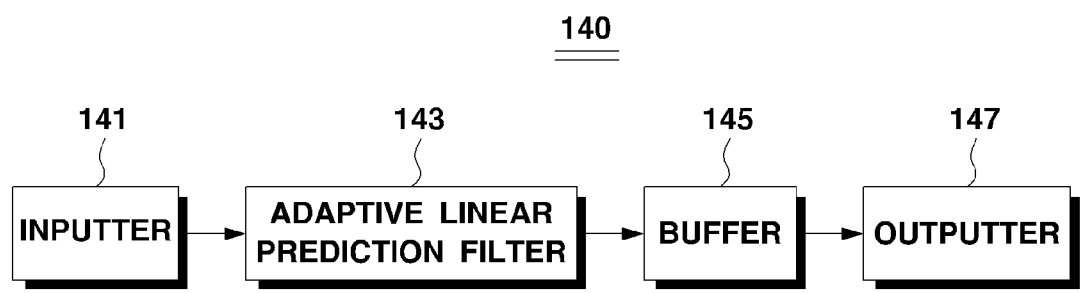
FIG. 2 is a detailed block diagram of a filter of FIG. 1.

Hereinafter, the above-described filter 140 will be explained in detail with reference to FIG. 2. FIG. 2 is a detailed block diagram of the filter 140 of FIG. 1. As shown in FIG. 2, the filter 140 includes an inputter 141, an adaptive linear prediction filter 143, a buffer 145, and an outputter 147.

The inputter 141 receives the ECG signal which has been converted into the digital signal by the ADC 130, and transmits the ECG signal to the adaptive linear prediction filter 143.

The adaptive linear prediction filter 143 removes the baseline drift noise which exists in the ECG signal input through the inputter 141 based on an LMS algorithm.

The buffer 145 is a space that temporarily stores the filtered ECG signal which is output from the adaptive linear prediction filter 143.

The outputter 147 extracts the ECG signals when the ECG signals are stored in all of the storage spaces of the buffer 145 (a buffer full state), and transmits the ECG signals to the RF module 150.

Figure 3:
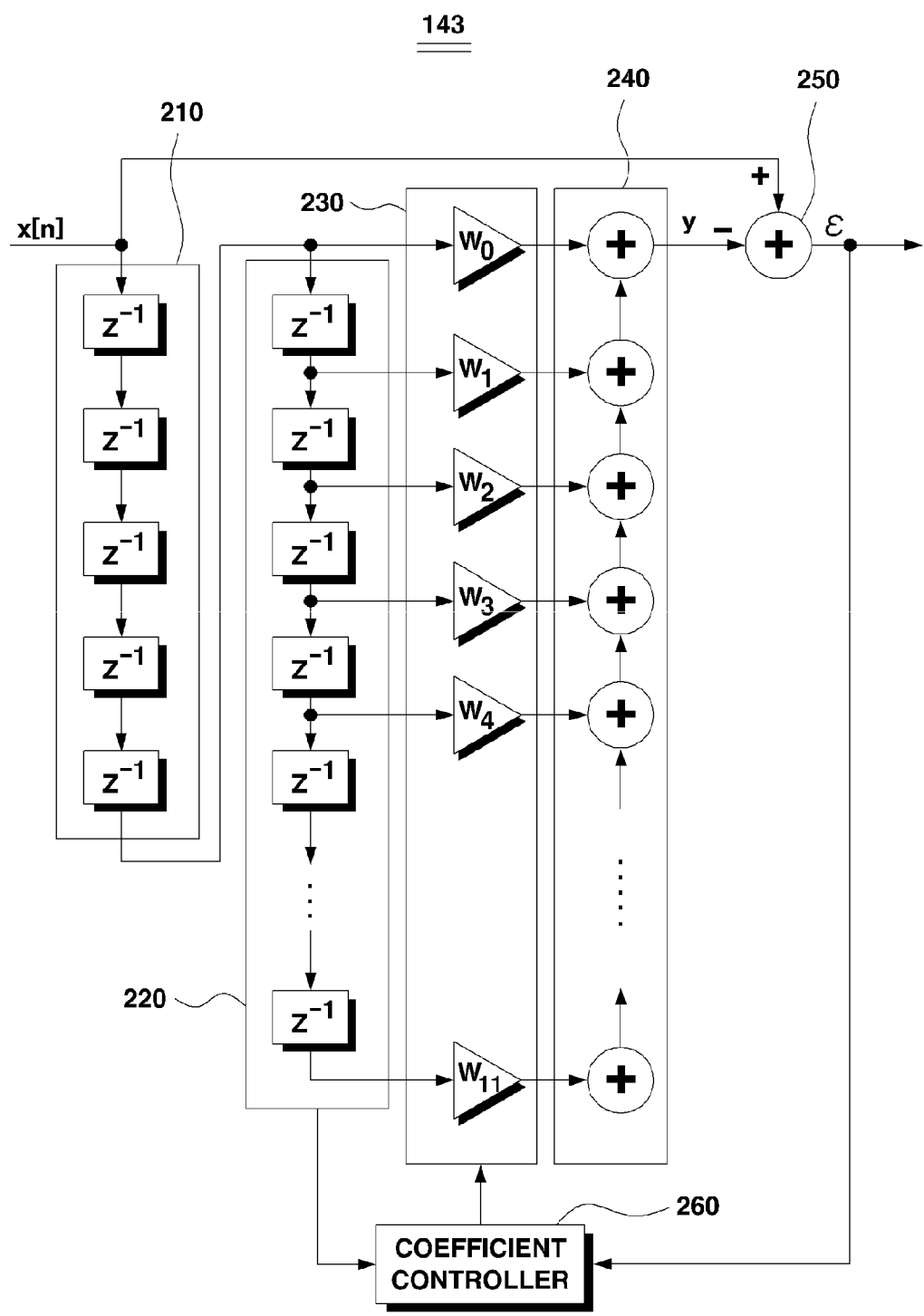
FIG. 3 is a detailed block diagram of an adaptive linear prediction filter of FIG. 2.

Hereinafter, the adaptive linear prediction filter of FIG. 2 will be explained in detail with reference to FIG. 3. FIG. 3 is a detailed block diagram of the adaptive linear prediction filter 143 of FIG. 2.

As shown in FIG. 3, the adaptive linear prediction filter 143 includes a sub delayer 210, a main delayer 220, a gain unit 230, an adder 240, a subtractor 250, and a coefficient controller 260.

The sub delayer 210 includes 5 delayers ($Z^{-1}$) and the main delayer 220 includes 12 delayers ($Z^{-1}$). The ECG signal (x[n]) which is input to the adaptive linear prediction filter 143 is shifted to the delayers ($Z^{-1}$) of the main delayer 220 through the delayers ($Z^{-1}$) of the sub delayer 210 in sequence.

The number of delayers ($Z^{-1}$) of the sub delayers 210 is smaller than the number of delayers ($Z^{-1}$) of the main delayer 220.

The delayers 210 and 220 are divided into the sub delayer 210 and the main delayer 220 in order to eliminate interrelationship between the noise of the ECG signal which is input to the adaptive linear prediction filter 143, and the noise of the ECG signals which are temporarily stored in the main delayer 220 when the coefficient is updated.

The gain unit 230 includes 12 amplifiers, and multiplies the 12 ECG signals which have been output from the sub delayer 210 and temporarily stored in the main delayer 220 by corresponding coefficients ($w_0, w_1, w_2, w_3, w_4, \ldots, w_{11}$), and outputs the ECG signals.

The adder 240 adds up the 12 ECG signals which have been multiplied by the coefficients ($w_0, w_1, w_2, w_3, w_4, \ldots w_{11}$) in the gain unit 230. The added ECG signal (y) which is output from the adder 240 is stored in the buffer 145 as output from the adaptive linear prediction filter 143.

The subtractor 250 subtracts the filtered ECG signal (y) which is the output from the adder 240 from the ECG signal (x[n]) which is input to the adaptive linear prediction filter 143, and generates an error signal ($\epsilon$).

The coefficient controller 260 updates the coefficients ($w_0, w_1, w_2, w_3, w_4, \ldots, w_{11}$) of the gain unit 230 using the error signal ($\epsilon$) which is output from the subtractor 250 and the 12 ECG signals which are temporarily stored in the main delayer 220.

Specifically, the coefficient controller 260 updates the coefficients ($w_0, w_1, w_2, w_3, w_4, \ldots, w_{11}$) of the gain unit 230 so that the error signal ($\epsilon$) can be minimized. The coefficient controller 260 may predict future output based on the past input by minimizing the error between the output which is sufficiently delayed by the delayers ($Z^{-1}$) of the sub delayer 210 and the main delayer 220, and the input ECG signal that is not delayed. In other words, the coefficient controller 260 may predict the future output using the delayed input and output the same output as an input waveform.

The filtering process of the adaptive linear prediction filter 143 of FIG. 3 will be explained in detail with reference to FIG. 4.

Figure 4:
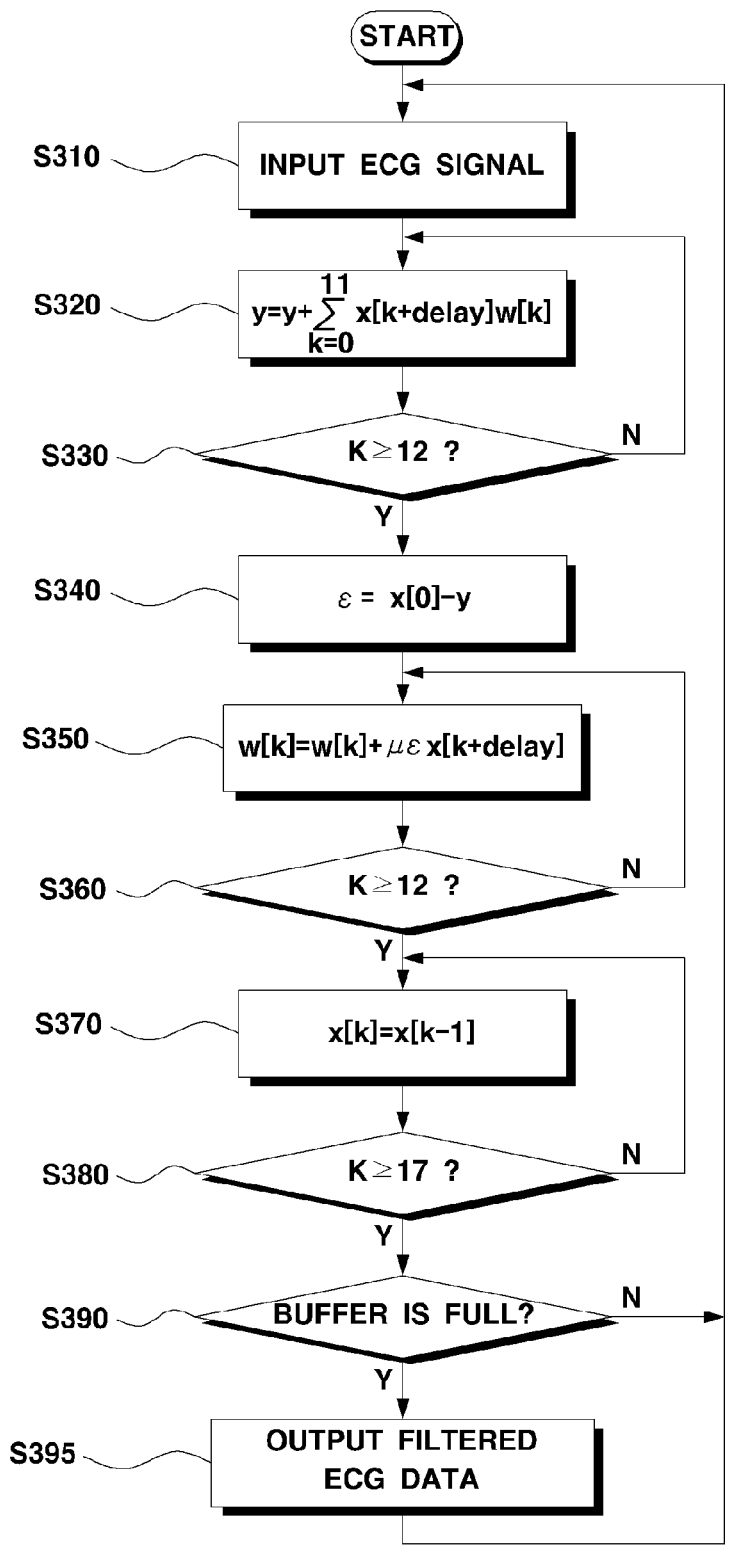
FIG. 4 is a flowchart to illustrate a filtering process of the adaptive linear prediction filter of FIG. 3.

As shown in FIG. 4, an ECG signal is input to the adaptive linear prediction filter 143 and delayed first, and is temporarily stored in sequence and shifted in the delayers ($Z^{-1}$) constituting the sub delayer 210 and the main delayer 220 (S310).

Then, the gain unit 230 multiplies the 12 ECG signals which are temporarily stored in the delayers ($Z^{-1}$) constituting the main delayer 220 in operation S310 by corresponding coefficients ($w_0, w_1, w_2, w_3, w_4, \ldots, w_{11}$), and the adder 240 adds up the 12 ECG signals which have bee multiplied by the corresponding coefficients ($w_0, w_1, w_2, w_3, w_4, \ldots, w_{11}$) (S320 and S330).

Operation S320 may be expressed by following equation 1:

$$y = y + \sum_{k=0}^{11} x[k+\text{delay}]w[k] \quad \text{[Equation 1]}$$

wherein delay is a number of delayers ($Z^{-1}$) constituting the sub delayer 210 and is 5 in the present exemplary embodiment.

Then, the subtractor 250 subtracts the filtered ECG signal (y) which is the output from the adder 240 from the ECG signal (x[0]) which is input to the adaptive linear prediction filter 143 most recently, and generates an error signal ($\epsilon$) (S340).

Next, the coefficient controller 260 updates the coefficients ($w_0, w_1, w_2, w_3, w_4, \ldots, w_{11}$) of the gain unit 230 using the error signal ($\epsilon$) which is generated in operation S340 and the 12 ECG signals (x[k+delay]) which are temporarily stored in the main delayer 220 (S350 and S360).

Operation S350 may be expressed by following equation 2:

$$w[k]=w[k]+\mu\epsilon x[k+\text{delay}] \quad \text{[Equation 2]}$$

wherein $\mu$ is a convergence constant and may be experimentally determined.

After that, an ECG signal is newly input, and is delayed and shifted in sequence by 17 delayers ($Z^{-1}$) of the sub delayer 210 and the main delayer 220 (S370 and S380).

On the other hand, when the filtered ECG data (y) is stored in all of the storage spaces of the buffer 145 (S390), the outputter 147 extracts the filtered ECG data and transmits the same to the RF module 150 (S395).

The number of delayers ($Z^{-1}$) constituting the sub delayer 210 and the main delayer 220 of the adaptive linear prediction filter 143 may be determined according to properties of the noise or other specifications.

The foregoing exemplary embodiments and advantages are merely exemplary and are not to be construed as limiting the present inventive concept. The exemplary embodiments can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An ElectroCardioGram (ECG) sensing apparatus comprising:
   an ECG sensor configured to
      measure ECG by using an electrode adapted to be located on a human body, and
      generate an ECG signal based on the measured ECG;
   a pre-processor configured to perform filtering and amplification with respect to the ECG signal which is generated by the ECG sensor;
   an analog-digital converter (ADC) configured to convert the ECG signal which is output from the pre-processor, from an analogue format into a digital format;
   a filter configured to
      filter the ECG signal converted by the ADC, and
      filter a baseline drift noise which is caused by motion and breathing of the human body; and
   a communication module configured to wirelessly transmit the ECG signal which is filtered by the filter,
   wherein the filter comprises:
      an inputter configured to receive the ECG signal which is converted into the digital signal by the ADC;
      an adaptive linear prediction filter configured to remove the baseline drift noise which exists in the ECG signal input to the inputter;
      a buffer configured to temporarily store the filtered ECG signal which is output from the adaptive linear prediction filter; and
      an outputter configured to transmit the ECG signal temporarily stored in the buffer to the communication module, and
   wherein the adaptive linear prediction filter comprises:
      a sub delayer which comprises a plurality of delayers configured to shift the ECG signal input to the inputter in sequence;
      a main delayer which comprises a plurality of delayers configured to shift the shifted ECG signals output from the sub delayers in sequence;
      a gain unit configured to multiply the ECG signals temporarily stored in the delayers of the main delayer by corresponding coefficients, and output the multiplied ECG signals; and an adder configured to add up all of the outputs of the gain unit and generate the filtered ECG signal.

2. The ECG sensing apparatus as claimed in claim 1, wherein the filter does not use an additional reference signal other than the ECG signal that is input from the ADC.

3. The ECG sensing apparatus as claimed in claim 1, wherein a number of delayers provided in the sub delayer is smaller than a number of delayers provided in the main delayer.

4. The ECG sensing apparatus as claimed in claim 1, wherein the adaptive linear prediction filter further comprises:
- a subtractor configured to subtract the filtered ECG signal which is generated by the adder from the ECG signal input to the inputter, and generate an error signal; and
- a coefficient controller configured to update the coefficients of the gain unit using the error signal which is output from the subtractor and the ECG signals which are temporarily stored in the delayers of the main delayer.

5. The ECG sensing apparatus as claimed in claim 4, wherein the coefficient controller is configured to update the coefficients of the gain unit using the following equation:

$$w[k]=w[k]+\mu\epsilon x[k+\text{delay}]$$

wherein $w[k]$ is a coefficient of a k-th amplifier of the gain unit, $\mu$ is a convergence constant, $\epsilon$ is the error signal, $x[k+\text{delay}]$ is the ECG signal which is temporarily stored in a k-th delayer of the main delayer, and delay is a number of delayers provided in the sub delayer.

6. A method for sensing ElectroCardioGram (ECG), the method comprising:
- measuring ECG by using an electrode adapted to be located on a human body and generating an ECG signal based on the measured ECG;
- pre-processing to perform filtering and amplification with respect to the ECG signal which is generated in the generating operation;
- converting the ECG signal which is output in the pre-processing operation from an analogue format into a digital format;
- filtering the converted ECG signal by removing a baseline drift noise from the converted ECG signal, wherein the baseline drift noise is caused by which is converted in the converting operation and filtering a baseline drift noise which is caused by the human body; and
- wirelessly transmitting the ECG signal which is filtered in the filtering operation, wherein said filtering the converted ECG signal comprising:
- delaying the converted ECG signal by shifting the converted ECG signal in sequence;
- delaying again the delayed ECG signal by shifting the delayed ECG signal in sequence;
- multiplying the double delayed ECG signal by one or more corresponding coefficients; and
- adding one or more multiplied ECG signals to generate the filtered ECG signal.

* * * * *